(12) United States Patent
Neame

(10) Patent No.: US 8,104,476 B2
(45) Date of Patent: Jan. 31, 2012

(54) MEDICO-SURGICAL TUBE ASSEMBLIES

(75) Inventor: Simon Neame, Broadstairs (GB)

(73) Assignee: Smiths Group plc, London (GB)

( * ) Notice: Subject to any disclaimer, the term of this patent is extended or adjusted under 35 U.S.C. 154(b) by 548 days.

(21) Appl. No.: 12/308,569

(22) PCT Filed: Jun. 26, 2007

(86) PCT No.: PCT/GB2007/002389
§ 371 (c)(1),
(2), (4) Date: Dec. 18, 2008

(87) PCT Pub. No.: WO2008/003929
PCT Pub. Date: Jan. 10, 2008

(65) Prior Publication Data
US 2009/0308397 A1  Dec. 17, 2009

(30) Foreign Application Priority Data
Jul. 1, 2006 (GB) .................................. 0613047.0

(51) Int. Cl.
*A61M 16/00* (2006.01)
(52) U.S. Cl. .............................. 128/207.17; 128/200.26
(58) Field of Classification Search ............. 128/207.14, 128/207.17, DIG. 26, 200.26, 207.15; 604/174, 604/178, 165.01–165.04
See application file for complete search history.

(56) References Cited

U.S. PATENT DOCUMENTS

| 5,026,352 | A | | 6/1991 | Anderson |
| 5,549,657 | A | * | 8/1996 | Stern et al. ..................... 604/537 |
| 5,803,079 | A | * | 9/1998 | Rogers et al. ............ 128/207.14 |
| 6,134,477 | A | * | 10/2000 | Knuteson ....................... 607/115 |
| 6,755,191 | B2 | * | 6/2004 | Bertoch et al. ........... 128/200.26 |

FOREIGN PATENT DOCUMENTS

| EP | 1382861 | 1/2004 |
| WO | 2006/087513 | 8/2006 |

* cited by examiner

*Primary Examiner* — Fenn Mathew
(74) *Attorney, Agent, or Firm* — Louis Woo

(57) ABSTRACT

An adjustable flange for a tracheostomy tube has a locking assembly (25) with two C shape clamp arms (26) and (27) hinged together at one end (28). A lever (50) with a threaded stem (51) extends through the opposite end of one arm (27) and into a threaded aperture (32) in the other arm (26). When the handle (55) of the lever (50) is inclined out of the plane of the locking assembly (25) it can be slid freely along the tracheostomy tube (1) for positioning. The locking assembly (25) is locked in position by rotating the handle (55) down to lie in the plane of the locking assembly. The flange (20) has two wings (22) and (23) connected with a central plate (20) by webs (42) and (43) of reduced width so that the webs flex to allow the wings to be lifted readily.

8 Claims, 3 Drawing Sheets

MEDICO-SURGICAL TUBE ASSEMBLIES

This invention relates to medico-surgical tube assemblies of the kind including a tube and a locking assembly movable along a part at least of the length of the tube and lockable in position along the tube, the locking assembly extending in a plane laterally about the tube.

Medico-surgical tubes, such as tracheostomy tubes, are commonly provided with a flange to secure the tube to the patient's body. In the case of a tracheostomy tube, the flange is positioned close to the surface of the neck where the tube enters the tracheostomy, a tape is threaded through openings in the flange and fastened around the neck. For most patients, a comfortable fit can be achieved using one of a range of several different size tubes, each having a flange mounted at a fixed location along the tube suitable for patients having an average anatomy. There are, however, some situations where a fixed flange is not suitable, such as, for example, in obese patients where tissue between the neck surface and the trachea is very thick. In these situations, it is preferable for the flange to be movable along the tube to the ideal position and to be lockable in that position. Tubes with adjustable flanges are described in, for example, U.S. Pat. No. 5,026,352, U.S. Pat. No. 4,249,529, U.S. Pat. No. 4,449,527, U.S. Pat. No. 4,498,903, U.S. Pat. No. 4,530,354, U.S. Pat. No. 4,530,354, U.S. Pat. No. 4,649,913, U.S. Pat. No. 4,683,882, U.S. Pat. No. 4,774,944, WO80/02645, WO84/03217, U.S. Pat. No. 4,278,081 and PCT/GB06/000268. It is, however, difficult to achieve a secure fastening of the flange to the tube in a simple manner whilst also enabling the flange to be moved and secured easily, especially where the tube is wet and slippery. It can also be advantageous for it to be readily apparent that the flange has been securely locked in position.

It is an object of the present invention to provide an alternative medico-surgical tube.

According to the present invention there is provided a medico-surgical tube assembly of the above-specified kind, characterised in that the locking assembly includes a manually-operable lever having a handle portion movable between a first, unlocked position in which the handle lies at an angle to the plane of the locking assembly to a second, locked position in which the handle portion lies substantially parallel with the plane of the locking assembly.

The lever is preferably arranged to clamp two parts of the locking assembly together against opposite sides of the tube when the locking assembly is locked. The two parts of the locking assembly preferably have a plurality of deformable rings adapted to engage the outside surface of the tube. The two parts of the locking assembly are preferably of C shape and connected together by a living hinge. The lever may include a stem extending from the handle portion, the stem having a threaded portion engaging a threaded aperture in one part of the locking assembly such that when the stem is rotated by moving the handle portion the two parts of the locking assembly are moved together. The lever and locking assembly may have cooperating detents to retain the lever in the locked position. The locking assembly may include a flange by which the tube is secured with the neck of the patient, the flange having a central section and two wing sections attached integrally with the central section by respective webs, the webs having a reduced width compared with the central section and the wing sections so that the webs flex to allow the wing sections to be pulled forwardly for access to the region under the flange. The tube is preferably a tracheostomy tube.

A tracheostomy tube assembly according to the present invention will now be described, by way of example, with reference to the accompanying drawing, in which.

Figure 1:
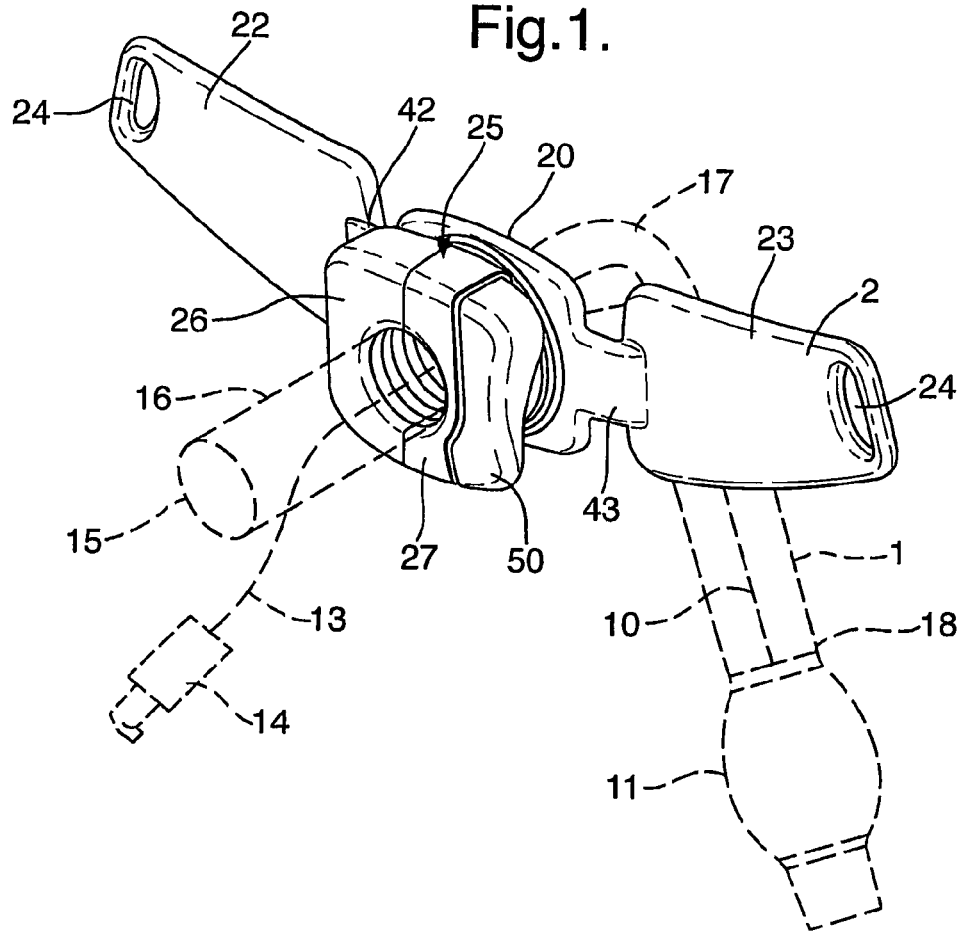
FIG. 1 is a perspective view of the assembly, showing the tube in phantom.

The tube assembly comprises a tube 1 (shown in phantom) and a flange 2 with a locking assembly 25, the flange being movable along the tube and lockable at different locations along its length.

The tube 1 is made of a conventional, bendable plastics material, such as PVC, polyurethane or silicone, is hollow with a circular section and has a smooth inner surface. The tube 1 may have a shaft reinforced with a helical wire or similar member. An inflation lumen 10 extends along the length of the tube in a small rib on its outside surface. At one end, the lumen 10 connects with the interior of a sealing cuff 11. Towards its other, rear end, the inflation lumen 10 connects with one end of an inflation line 13 the other end of which is connected with a pilot balloon and connector 14. The tube 1 has a machine end 15 adapted to be located outside the body and may be connected to patient breathing apparatus or left open to air. The shaft of the tube 1 comprises a straight machine end region 16, a curved intermediate region 17 and a straight patient end region 18 extending at substantially right angles to the patient end region. Alternative shape shafts are possible, such as shafts that are curved continuously along their length or shafts that have a natural straight shape but are highly flexible so that they can conform readily to the shape of the anatomy.

The flange 2 has a rectangular central plate 20 with a central circular aperture the diameter of which is such that the tube 1 is a close sliding fit within it. Two wings 22 and 23 extend from the central plate 20 on opposite sides. The two wings 22 and 23 are generally rectangular, being curved slightly along their length and are each formed with a lateral slot 24 towards their free end by which a tape, strap or the like can be secured to the wing. The two wings 22 and 23 are attached with the central plate 20 by respective flexure sections or webs 42 and 43 formed integrally with the plate and the wings. The webs 42 and 43 have a reduced width compared with the plate 20 and wings 22 and 23 to allow them to flex when the wings are pulled forwardly. This allows the wings to hinge when they are pulled forwardly after positioning, for access, observation or cleaning of the region under the flange. The reduced width of the webs 42 and 43 also allows some rotational movement between the wings and the central plate, and hence the tube. This helps reduce the torque applied to the patient. The flange is also arranged such that the rear, patient side of the wings 22 and 23 is set forwardly relative to the rear side of the central plate 20 by 1-2 mm so as to reduce pressure on the stoma site. The wings 22 and 23 are also designed to be relative large in area so as to help reduce pressure on any one part of the neck anatomy, which may help reduce pressure sores. The large size of the wings also reduces the risk of the flange becoming lost in the skin folds present in a larger neck mass.

Figure 3:
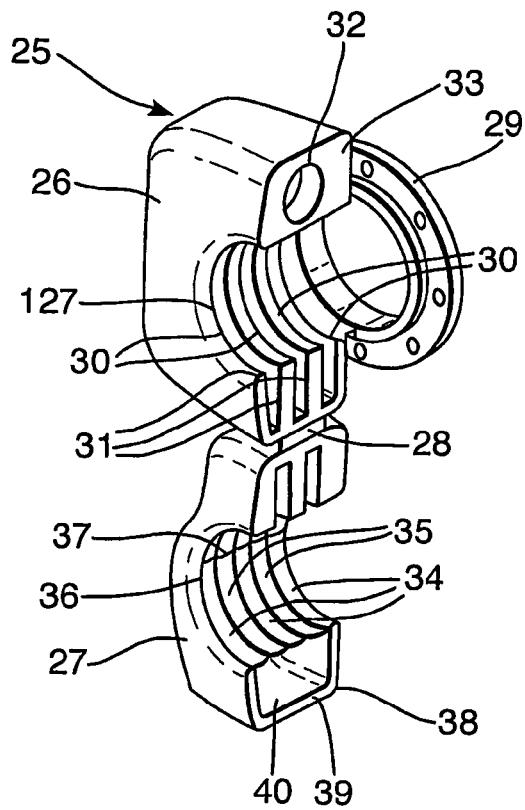
FIG. 3 is a perspective view from one side of the locking assembly opened out and without the lever.
Figure 4:
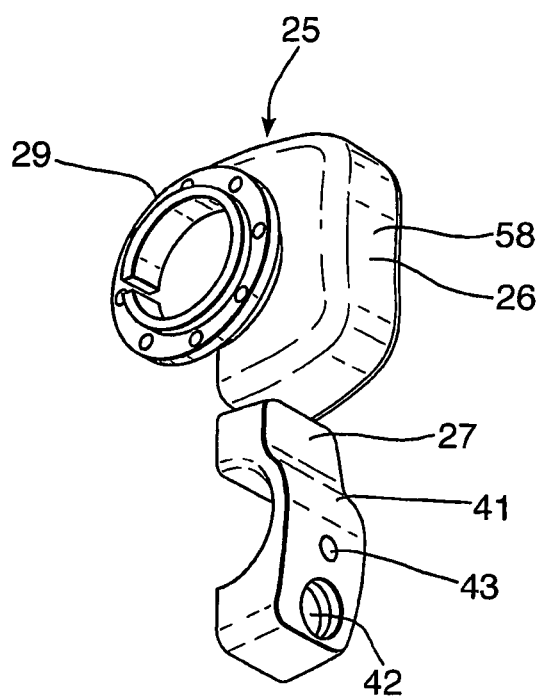
FIG. 4 is a perspective view of the locking assembly shown in FIG. 3 from an opposite side.

The locking assembly or clamp 25 is mounted centrally on the rear or machine face of the central plate 20. The clamp 25 has an integral moulded plastics component comprising arms 26 and 27 linked together at the lower edge by an integral flexible web or living hinge 28 (FIG. 3). The left-hand arm 26 is fixed with the central plate 20 by means of a circular mounting ring 29. The arm 26 has a C shape with a central semicircular recess 127 aligned with the aperture in the mounting ring 29. The recess 127 is formed with four rings 30 separated from one another axially by three channels 31 so that the rings are deformable and enhance the grip on the tube 1. The left-hand arm 26 has a threaded aperture 32 in its upper mating end face 33, the purpose of which will become apparent later. The other, right-hand arm 27 is similarly formed with three rings 34 and two channels 35 in a semicircular recess 36. The rings 34, however, are reduced in height midway across the arm 27 to form a longitudinally-extending groove 37 adapted to receive the inflation lumen 10 on the tube 1. The free end 38 of the right-hand arm 27 has a mating face 39 with a hollow cavity 40 opening to the outer surface 41 of the arm through a circular aperture 42. The outer surface 41 of the arm 27 is curved and is interrupted close to the aperture 42 by a detent recess 43, the purpose of which will become apparent later.

When the free arm 27 of the locking clamp 25 is folded up, as shown in FIG. 1, the clamp has a generally rectangular shape extending in a plane at right angles to the axis of the tube 1.

Figure 5:
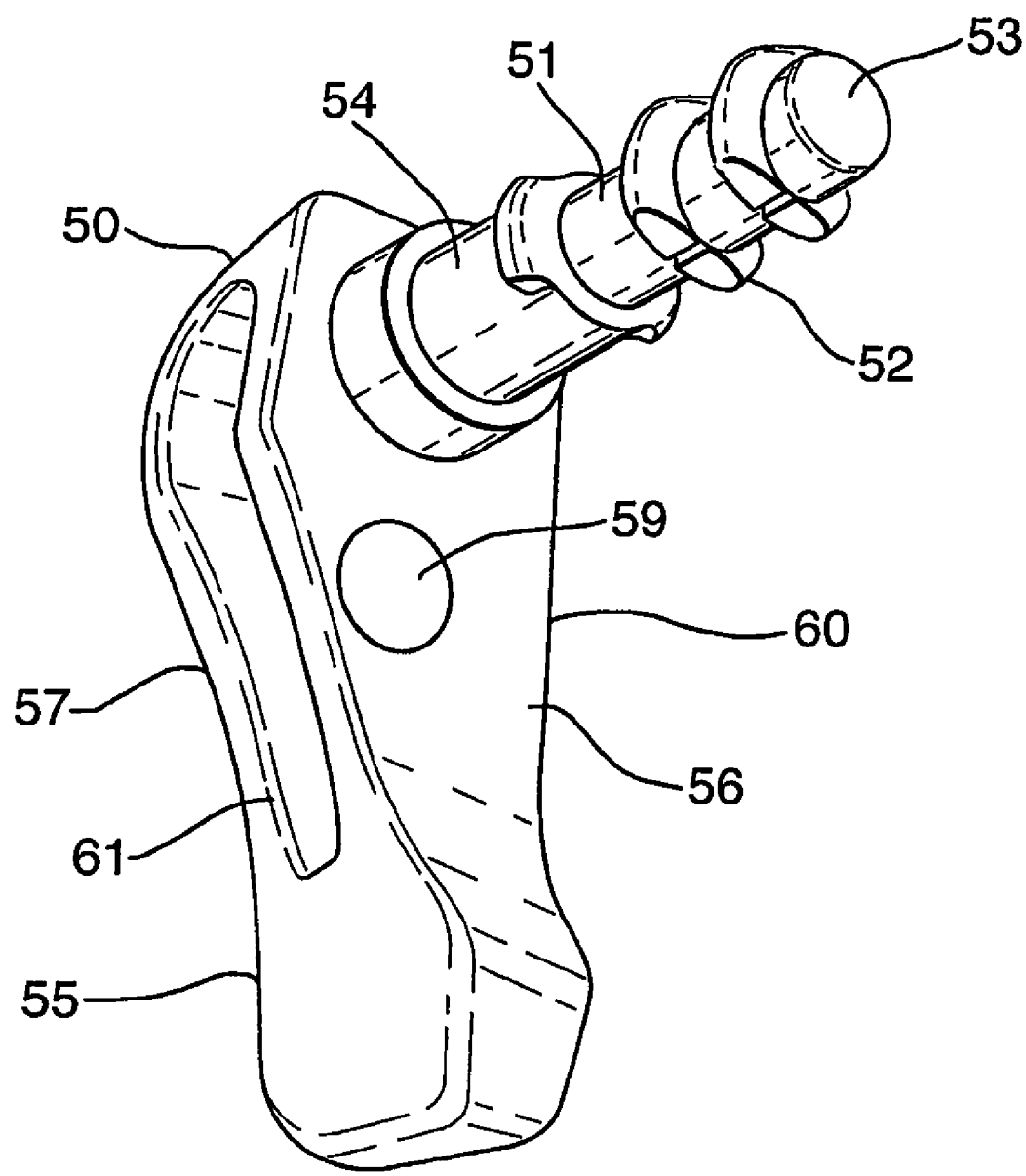
FIG. 5 is a perspective view of the locking lever.

The clamp 25 is completed by a locking lever 50, as shown in FIG. 5, of a rigid plastics material such as nylon. The lever 50 has a stem 51 of circular section and formed with a partial screw thread 52 towards its free end 53. The inner end 54 of the stem 51 is smooth. The stem 51 is attached and moulded integrally with one end of a handle 55, which extends at right angles to the stem. The shape of the handle 55 is chosen to match that of the clamp arms 26 and 27. The inner edge 56 of the handle 55 follows closely the outer edge of the right-hand arm 27; the outer edge 57 of the handle matches the outer edge 58 of the left-hand clamp arm 26. The inner edge 56 of the handle 55 is formed with a hemispherical detent protuberance 59 adjacent the stem 51 and located to align with the detent recess 43 on the right-hand arm 27. The front surface 60 of the handle 55 aligns with the front surface of the clamp arm 27 but its rear surface 61 tapers to a reduced thickness away from the stem so as to leave a gap for finger access between the handle and the central plate 20 when locked. The stem 51 of the lever 50 projects through the aperture 42 and the cavity 40 in the right-hand arm 27, with the threaded portion 52 of the stem engaged as a screw-fit in the threaded aperture 32 in the left-hand arm 26.

Figure 2:
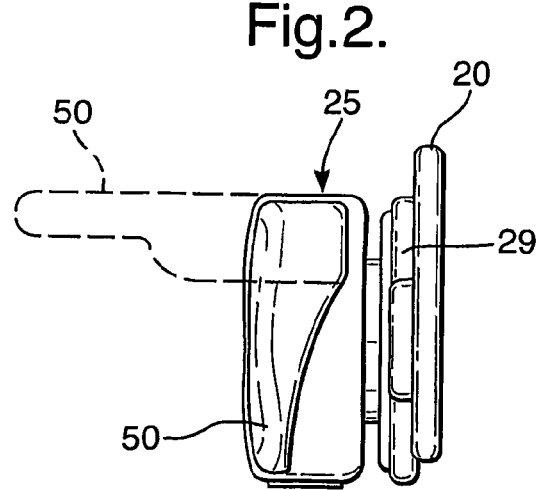
FIG. 2 is a side elevation view of the locking assembly showing the locked and unlocked positions of the lever.

The locking lever 50 is displaceable between an unlocked position and a locked position. In the unlocked position the handle 55 of the lever 50 projects rearwardly at an angle of between 90° and 180° to the plane of the clamp 25, as shown by the broken outline in FIG. 2 where it extends at 90°, that is, parallel to the tube 1. In this position, the free end 38 of the right-hand clamp arm 27 is held slightly separate from the left-hand arm 26 so that the clamp 25 does not exert any significant gripping force on the tube 1, and the flange 2 is free to slide along the length of the tube. In the locked position, the handle 55 extends downwardly parallel with the plane of the clamp 25 and the thread 52 on the stem 51 acts to pull the upper ends of the two arms 26 and 27 tightly towards one another, so that they securely grip the outside of the tube 1. The handle 55 is retained securely in this locked position against accidental displacement by engagement of the detent protuberance 59 on the handle in the detent recess 43 on the clamp arm 27. It can be seen, with the handle 55 folded down to the locked position, that the shape of the handle forms a continuation of the shape of the clamp arms 26 and 27. It is, therefore, readily apparent to the user that the clamp 25 is unlocked if the handle 55 is angled up out of the plane of the clamp.

In use, the handle 55 is rotated initially to the unlocked position so that the flange 2 can be slid along the tube 1. The user positions the flange 2 at the desired position along the tube 1, such as against graduation marks. He then rotates the handle 55 of the locking lever 50 down so that it lies parallel with the clamping arms 26 and 27 and so that the flange 2 is clamped firmly in position. The flange 2 can then be secured with the neck of the patient by means of a tape or the like in the usual way. Alternatively, the tube 1 could then inserted in the tracheostomy stoma with the flange 2 at a rear position. When the tube 1 had been correctly inserted, the flange 2 would be slid forwardly to abut the skin around the tracheostomy and then locked in position using the locking lever 50.

The invention is not confined to tracheostomy tubes but could be used with other medico-surgical tubes having a flange for supporting the tube where it emerges from the body.

The invention claimed is:

1. A medico-surgical tube assembly including a tube and a locking assembly movable along a part at least of the length of the tube and lockable in position along the tube, the locking assembly extending in a plane laterally about the tube, characterized in that the locking assembly includes a manually-operable lever having a stem and an elongate handle portion projecting laterally outwardly of the stem, that the handle portion is movable between a first, unlocked position to a second, locked position so as to rotate the stem and tighten the locking assembly about the tube, and that the handle portion projects at an angle from the plane of the locking assembly in the first, unlocked position and lies substantially parallel with the plane of the locking assembly in the second, locked position.

2. A medico-surgical tube assembly according to claim 1, in that the lever is arranged to clamp two parts of the locking assembly together against opposite sides of the tube when the locking assembly is locked.

3. A medico-surgical tube assembly according to claim 2, characterized in that the two parts of the locking assembly have a plurality of deformable rings adapted to engage the outside surface of the tube.

4. A medico-surgical tube assembly according to claim 1, characterized in that the two parts of the locking assembly are of C shape and are connected together by a living hinge.

5. A medico-surgical tube assembly according to claim 1, characterized in that the stem has a threaded portion engaging a threaded aperture in one part of the locking assembly such that when the stem is rotated by moving the handle portion the two parts of the locking assembly are moved together.

6. A medico-surgical tube assembly according to claim 1, characterized in that the lever and the locking assembly have cooperating detents to retain the lever in the locked position.

7. A medico-surgical tube assembly according to claim 1, characterized in that the locking assembly includes a flange by which the tube is secured with the neck of the patient, that the flange has a central section and two wing sections attached integrally with the central section by respective webs, and that the webs have a reduced width compared with the central section and the wing sections so that the webs flex to allow the wing sections to be pulled forwardly for access to the region under the flange.

8. A medico-surgical tube assembly according to claim 1, characterized in that the tube is a tracheostomy tube.

* * * * *